United States Patent
Klemm

(10) Patent No.: US 7,422,016 B2
(45) Date of Patent: Sep. 9, 2008

(54) ANTERIOR SUPPORT DEVICE

(75) Inventor: Kurt Klemm, Rhinelander, WI (US)

(73) Assignee: Pilgrim Innovations, LLC, Omro, WI (US)

( * ) Notice: Subject to any disclaimer, the term of this patent is extended or adjusted under 35 U.S.C. 154(b) by 370 days.

(21) Appl. No.: 10/427,108

(22) Filed: Apr. 30, 2003

(65) Prior Publication Data

US 2003/0183236 A1  Oct. 2, 2003

Related U.S. Application Data

(60) Continuation-in-part of application No. 10/180,621, filed on Jun. 26, 2002, which is a division of application No. 09/932,041, filed on Aug. 17, 2001, now Pat. No. 6,435,186.

(51) Int. Cl.
 *A61G 15/00* (2006.01)
(52) U.S. Cl. ............................ 128/845; 248/161
(58) Field of Classification Search ............... 128/845, 128/846; 5/623, 624, 646; 248/118, 118.1, 248/161
See application file for complete search history.

(56) References Cited

U.S. PATENT DOCUMENTS

| 135,435 | A | 2/1873 | Lyon |
| 2,038,806 | A | 4/1936 | Sellar .................... 155/134 |
| 2,519,771 | A | 8/1950 | Lacore .................... 155/165 |
| 3,216,767 | A | 11/1965 | Lutfy |
| 3,848,838 | A | 11/1974 | Thomas |
| 3,897,778 | A | 8/1975 | Forbes-Robinson et al. |
| 3,977,645 | A | 8/1976 | Deely |
| 4,397,374 | A | 8/1983 | Rumage et al. ............. 182/129 |
| 4,727,958 | A | 3/1988 | Botello |
| 4,917,343 | A | 4/1990 | Wainscott |
| 5,118,062 | A | 6/1992 | Archambault ............... 248/285 |
| 5,281,001 | A * | 1/1994 | Bergsten et al. ......... 297/411.24 |
| 5,295,728 | A | 3/1994 | Schaevitz |
| 5,545,177 | A | 8/1996 | Coseo ........................ 606/204 |
| 5,887,948 | A * | 3/1999 | Hannes ................... 297/411.35 |
| 6,102,344 | A | 8/2000 | Kasvin et al. |
| 6,138,970 | A * | 10/2000 | Sohrt et al. .............. 248/278.1 |

(Continued)

OTHER PUBLICATIONS

Kobo Chair, internet, http://www.kobochair.com/iframes/productinfo.html, 1 page, date printed Oct. 13, 2005.

(Continued)

*Primary Examiner*—Michael A. Brown
(74) *Attorney, Agent, or Firm*—Wilhelm Law Service; Thomas J. Conelly; Thomas D. Wilhelm

(57) ABSTRACT

The present invention is directed to a device which supports a user's spine while the user is in a forward bent position. The device includes a padded rest on which the user can lean while working in a forward bent position, and support structure enabling at least three of lateral adjustment of the rest along the projected perimeter of the work area, adjustment of the rest across the projected perimeter, height adjustment of the rest, and angular orientation of the rest. Since the user leans against the rest, the stresses otherwise normally experienced in the lower, middle and upper back are substantially attenuated. Attenuating such stress attenuates the pain experienced by the user as well as potentially extending his or her productive life.

14 Claims, 9 Drawing Sheets

U.S. PATENT DOCUMENTS

| | | | |
|---|---|---|---|
| 6,309,329 B2 | 10/2001 | Conner | 482/125 |
| 6,435,186 B1 | 8/2002 | Klemm | |
| 6,553,918 B2 | 4/2003 | Bieza | |
| 6,554,238 B1 | 4/2003 | Hibberd | |
| 6,629,944 B2 * | 10/2003 | Smart | 602/36 |
| 6,708,935 B2 * | 3/2004 | Smeed | 248/118 |
| 2002/0158492 A1 | 10/2002 | Ko et al. | |

OTHER PUBLICATIONS

AliMed, Medical & Ergonomic Products . . . Internet, www.alimed.com/ProductDetail.asp?style=73251; date printed Dec. 4, 2006.

Dentech Advance Stools, internet, http://www.dentechcorp.com/products/stools.html; p. 1-2, date printed Mar. 27, 2007.

Office Organix, Advanced Ergonomics @ Internet Prices, internet, www.officeorganix.com/NPAbstool.htm; pp. 1-5, date printed Mar. 19, 2007.

* cited by examiner

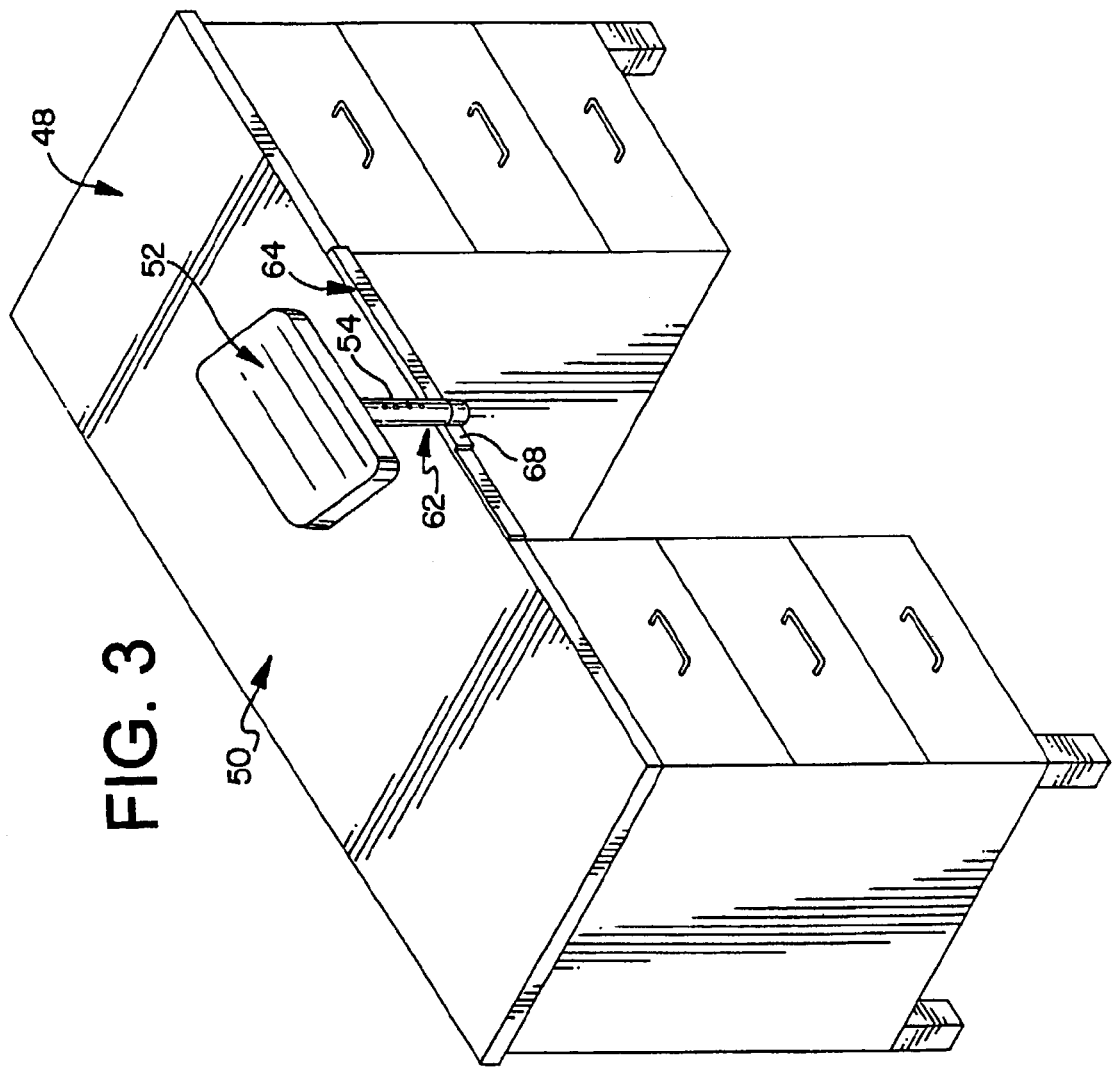
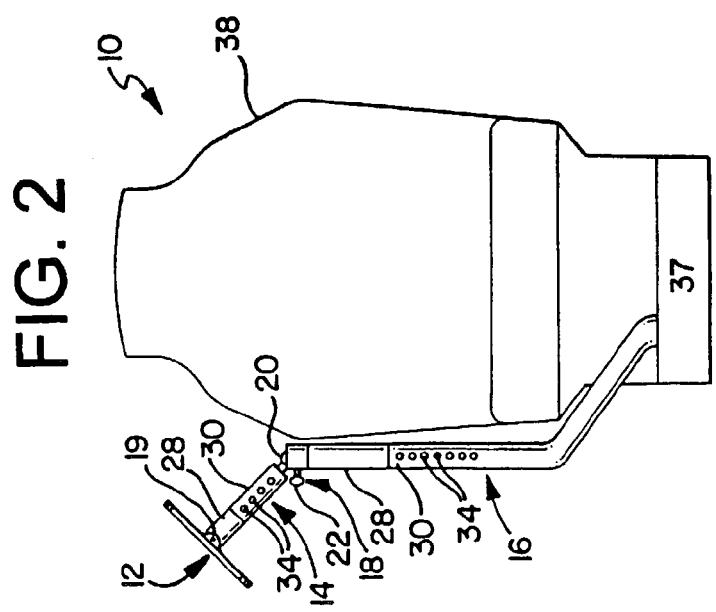

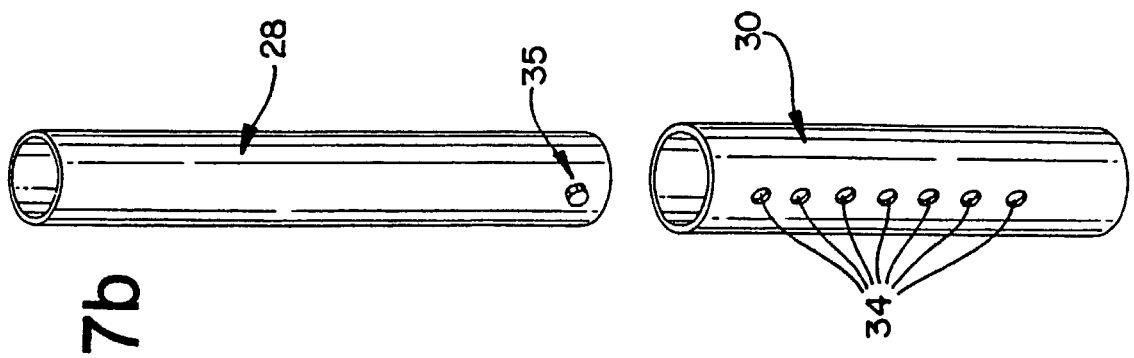
FIG. 7a  FIG. 7b
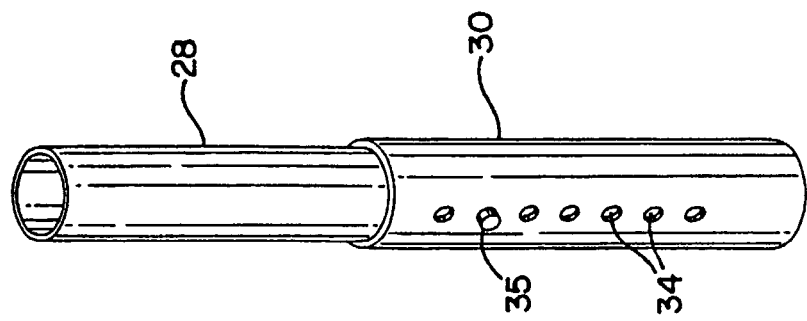
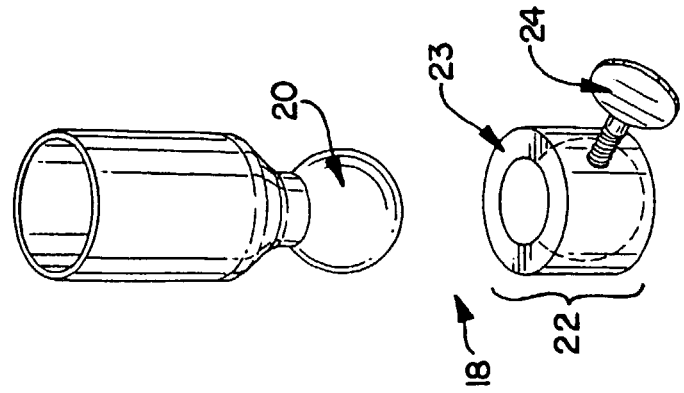
FIG. 6

DENTAL CHAIR
BACK VIEW
WITH LENGTH AND ANGLE ADJUSTMENTS

ANTERIOR SUPPORT DEVICE

RELATED APPLICATIONS

This application is a continuation-in-part application of U.S. patent application Ser. No. 10/180,621, filed on Jun. 26, 2002, which is a divisional of U.S. patent application Ser. No. 09/932,041, filed on Aug. 17, 2001, now U.S. Pat. No. 6,435,186, the entirety of the previously filed applications being incorporated herein by reference.

FIELD OF THE INVENTION

The present invention is directed generally to a support device and specifically to an anterior support device for use in the health care industry.

BACKGROUND OF THE INVENTION

Many individuals suffer from lower back pain and dysfunction brought about by their work environment or other daily activities. Repetitive or prolonged activities can be attributed as a major cause of this back pain and dysfunction. Effected individuals must drastically modify their work areas in order to continue their jobs. In many instances, people must choose another field of employment.

One such example is dentists. Dentists spend a good deal of their workday leaning over patients, in a forward bent position. This position contributes to posterior disc dysfunction, which leads to back pain and disability. For dentists, back pain is one of the leading causes of early retirement.

To alleviate such back pain, some individuals turn to physical therapy. Others attempt to support their backs while on the job by using braces and cushions that are intended to support the spine in a normal, anatomical position. These devices, however, are designed to support the individual from the rear and thus are not effective for dentists and similar professionals who must be in a forward, bent position as a fundamental part of their work.

Thus, there is a need in the art for a device that supports an individual's spine while the individual is in a forward bent position.

There is a further need in the art for a device that decreases the stress on the lower, mid, and upper back experienced by an individual while in a forward bent position.

There is yet a further need in the art for a device that extends the productive life of individuals who perform repetitive or prolonged activities as part of their employment or daily activities.

SUMMARY OF THE INVENTION

The present invention meets the needs of the prior art by providing a device which supports an individual's spine while the individual is in a forward bent position. The device includes a padded rest on which an individual can lean while working in a forward bent position and support structure for adjusting the angle, height, and position of the device. Since the individual leans against the rest, the stresses experienced in the lower, middle, and upper back are substantially decreased. Reducing such stress decreases the pain experienced by the individual as well as extends his or her productive life.

BRIEF DESCRIPTION OF THE DRAWINGS

FIG. 2 is a front view of the device shown in FIG. 1.

FIG. 3 is a perspective view of an alternate embodiment of the present invention in use with a desk.

FIG. 6 is a partially exploded, perspective view of the coupler used in the present invention.

FIGS. 7a and 7b are perspective views of the telescoping feature of the present invention.

DETAILED DESCRIPTION OF THE ILLUSTRATED EMBODIMENTS

Figure 1:
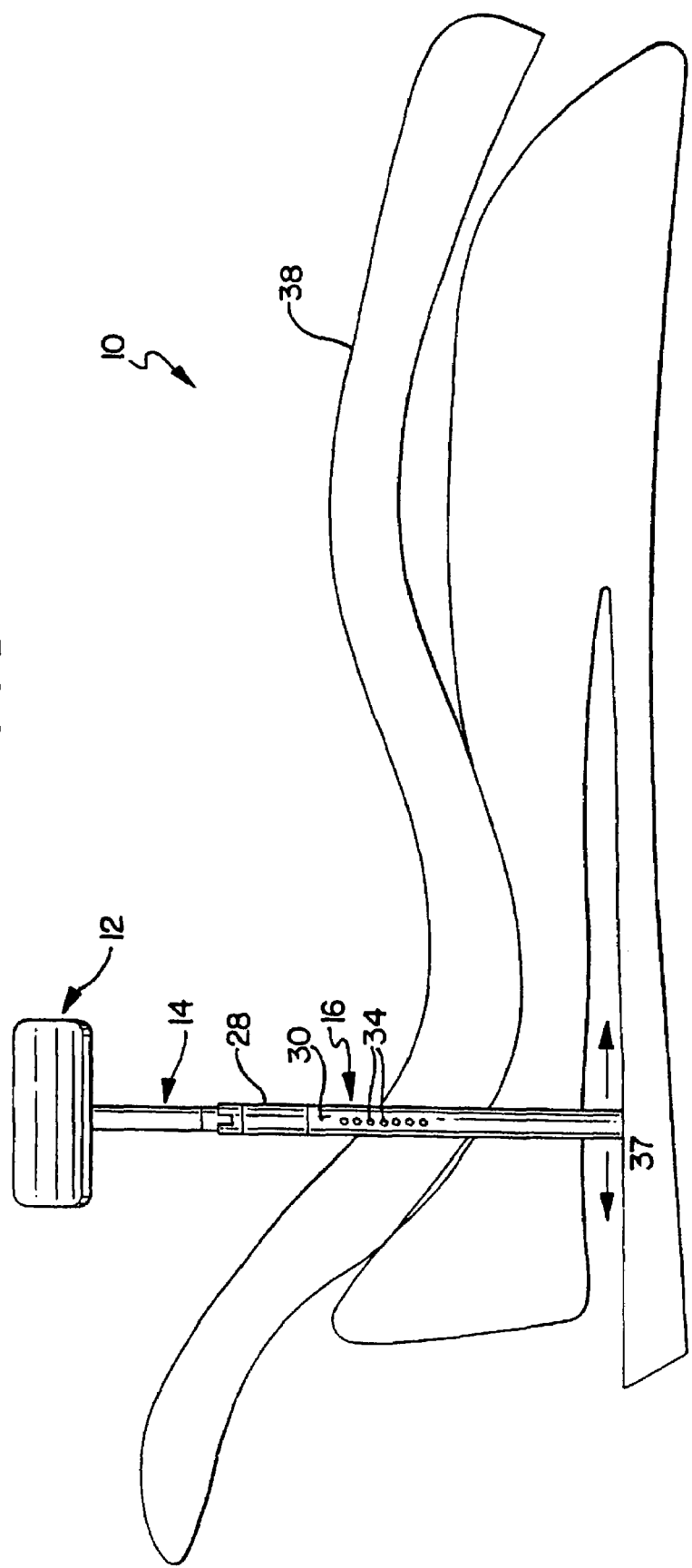
FIG. 1 is a perspective view of the present invention mounted adjacent a dentist's chair.

As depicted in the figures, the device 10 of the present invention generally includes a padded rest 12, an angled bracket 14, and an upright bracket 16. The padded rest 12 can pivot with respect to the angled bracket 14. This pivoting is enabled due to the presence of a single or multi-axial pivot device 19, as depicted in FIG. 2.

As can be best seen from FIG. 2, the bracket 14 extends at an angle from the upright bracket 16 so that the rest 12 is positioned to support the practitioner near the patient. To accomplish this, a coupler 18 is provided between the angled bracket 14 and the upright bracket 16 to allow the rest 12 to be tilted in any direction. Once the angular position of the bracket 14 with respect to the upright bracket 16 is adjusted to the desired position, the coupler 18 can be locked so as to hold the angled bracket 14 in that desired position.

Preferably, the coupler 18 takes the form of a ball swivel 20 having a screw pivot 22, as shown in detail in FIG. 6. The pivot 22 comprises a retainer 23 into which the ball end of the bracket is inserted and a screw tightener 24 for locking the bracket in the desired position.

Brackets 14 and 16 can be adjustable in length so that the distance of the rest 12 from the patient can be varied. Although the figures depict both brackets as being adjustable in length, the present invention does contemplate some embodiments wherein only one of brackets 14 and 16 is adjustable. To enable this adjustability, at least one of the brackets 14, 16 comprises a first bracket member 28 carrying a spring-loaded pin lock 35 and a second bracket member 30 including a plurality of adjusting holes 34. The details of this feature can be seen in FIGS. 7a and 7b. The first member 28 mates with, and telescopes with respect to, the second member 30 in a conventional manner of telescoping elements, wherein pin lock 35 is advanced along the length of second member 30 in such orientation of the first and second members 28, 30 that pin 35 does not come into alignment with any of holes 34. This telescoping allows the overall length of the respective bracket to be adjusted. Once the desired length of the bracket is obtained, the first and/or second members 28, 30 are re-oriented, again in a conventional manner such as by relative rotation, to bring pin 35 into alignment with one of holes 34, whereupon pin 35 springs into the respective hole 34 of the second bracket member 30, as shown in FIG. 7a. The pin 35 functions to lock bracket member 28 at the desired length with respect to bracket member 30. Thus, the overall length of the device can be varied by adjusting the length of one or both of brackets 14, 16.

Although not shown in FIGS. 7a and 7b, member 28 is provided with two spring loaded pin locks 35, one on each side of the member. Similarly, member 30 is provided with two arrays of adjusting holes 34, the arrays being 180 degrees apart around the perimeter of member 30. Therefore, the member 28 is held at the desired length by the interaction of both pin locks 35 with their respective arrays of adjusting holes 34. This further ensures that the bracket remains at the desired length.

Figure 8:
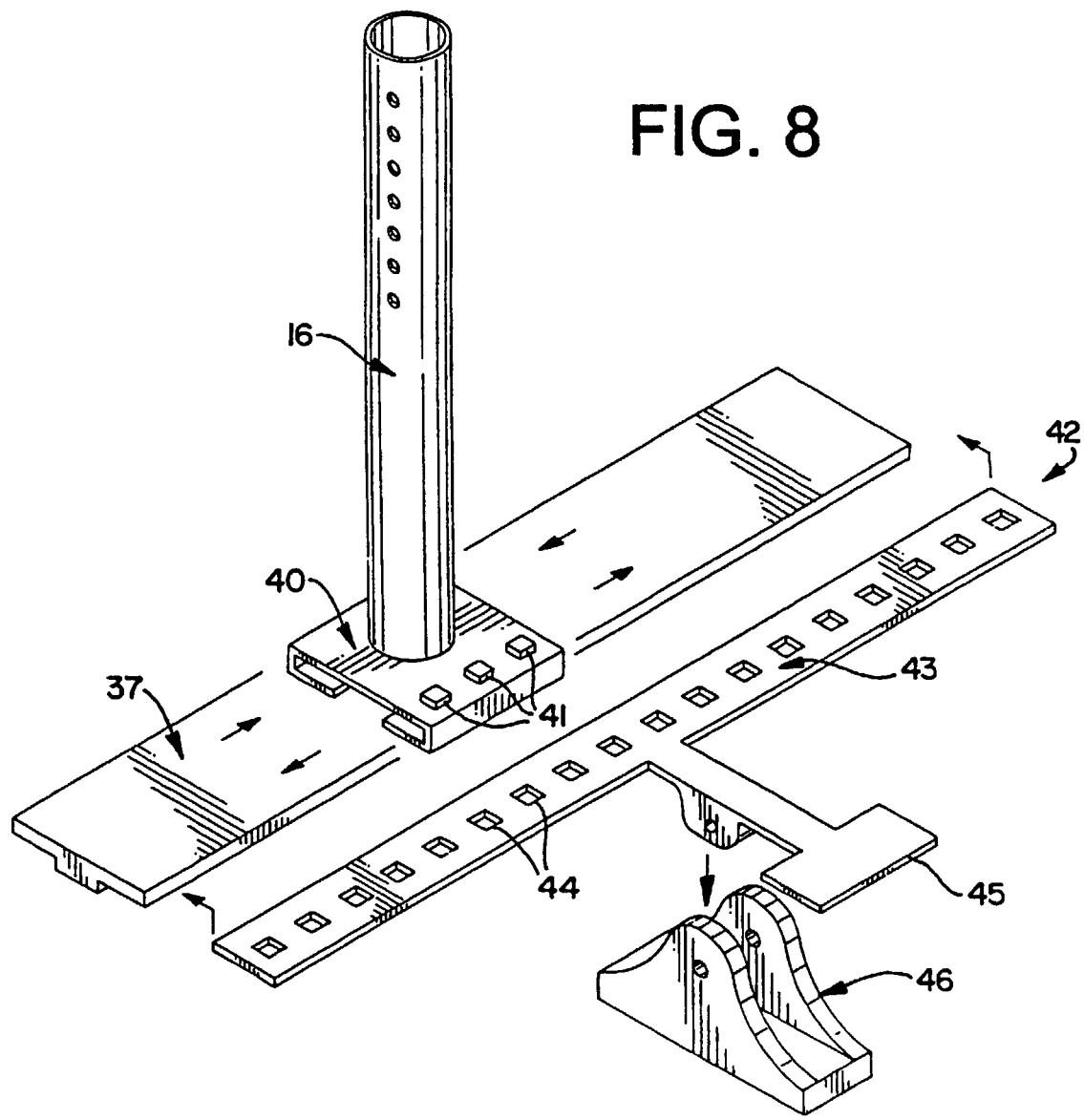
FIG. 8 is a partially exploded, perspective view of the coupling and locking mechanisms of the present invention for use with a dentist's chair.

As can be seen in FIGS. 1 and 2, the lower end of the bracket 16 is mounted to a track 37 which is positioned adjacent the base of the dental chair 38. Referring to FIG. 8, the lower end of the bracket 16 is provided with a slide plate 40 for coupling or riding along the track 37, the slide plate 40 including raised locking pins 41. The coupling of the bracket 16 along the track 37 enables the device to be moved along the base of the chair 38.

To lock the bracket 16 in the desired position along the track 37, a foot-controlled lock 42 is provided. Lock 42 comprises a spring-loaded locking bar 43 and a pivot mounting 46. The locking bar 43 includes a series of locking holes 44 and a footplate 45 extending from the bar. When the bracket 16 is in the locked position, the locking bar 43 is positioned above the slide plate 40, with ones of the locking holes 44 engaging the raised locking pins 41 of the slide plate 40. To release the bracket 16 from the locked position, the user steps down on the footplate 45, thereby causing the locking bar 43 to pivot about the mounting 46. This pivoting results in the locking pins 41 disengaging from the locking holes 44. The bracket 16 can then be moved to a new position along the track 37 where respective ones of holes 44 are positioned above pins 41, and in alignment with pins 41. To lock the bracket 16 in the new position, the professional merely releases the footplate 45. The foot plate 45 is biased into contact with the slide plate 41, the holes 44 again engaging the underlying pins 41. Thus, the position of the device 10 can be changed to accommodate the preference of the professional or the particular patient.

The padded rest 12 can be used by a professional such as a dentist or a dental hygienist to lean over a patient while working on the patient. Since the back of the professional is supported while in this bent position, the stress experienced by the professional in his or her lower, mid, and/or upper back is reduced. Because the source of the support is anterior, the professional can assume any degree of forward lean to accomplish the required task and still be supported.

Due to bracket 14, the padded rest 12 can be tilted in any direction to accommodate a particular body type or gender. The amount of padding is variable to allow the professional to change the contact points of the rest. Depending upon the comfort and preference of the professional, the rest can contact the professional in the abdominal, chest, or anterior shoulder areas.

To use the present invention, the professional adjusts the angle of bracket 14, the height of bracket 14 and/or bracket 16, and the position of bracket 16 with respect to the dental chair 38. Then the professional can lean forward against rest 12, while working on the patient. Alternately, the professional can sit in a chair and lean against rest 12 to work on the patient. Because the professional is allowed to lean against rest 12, the back stresses experienced by the professional are reduced.

Figure 9:
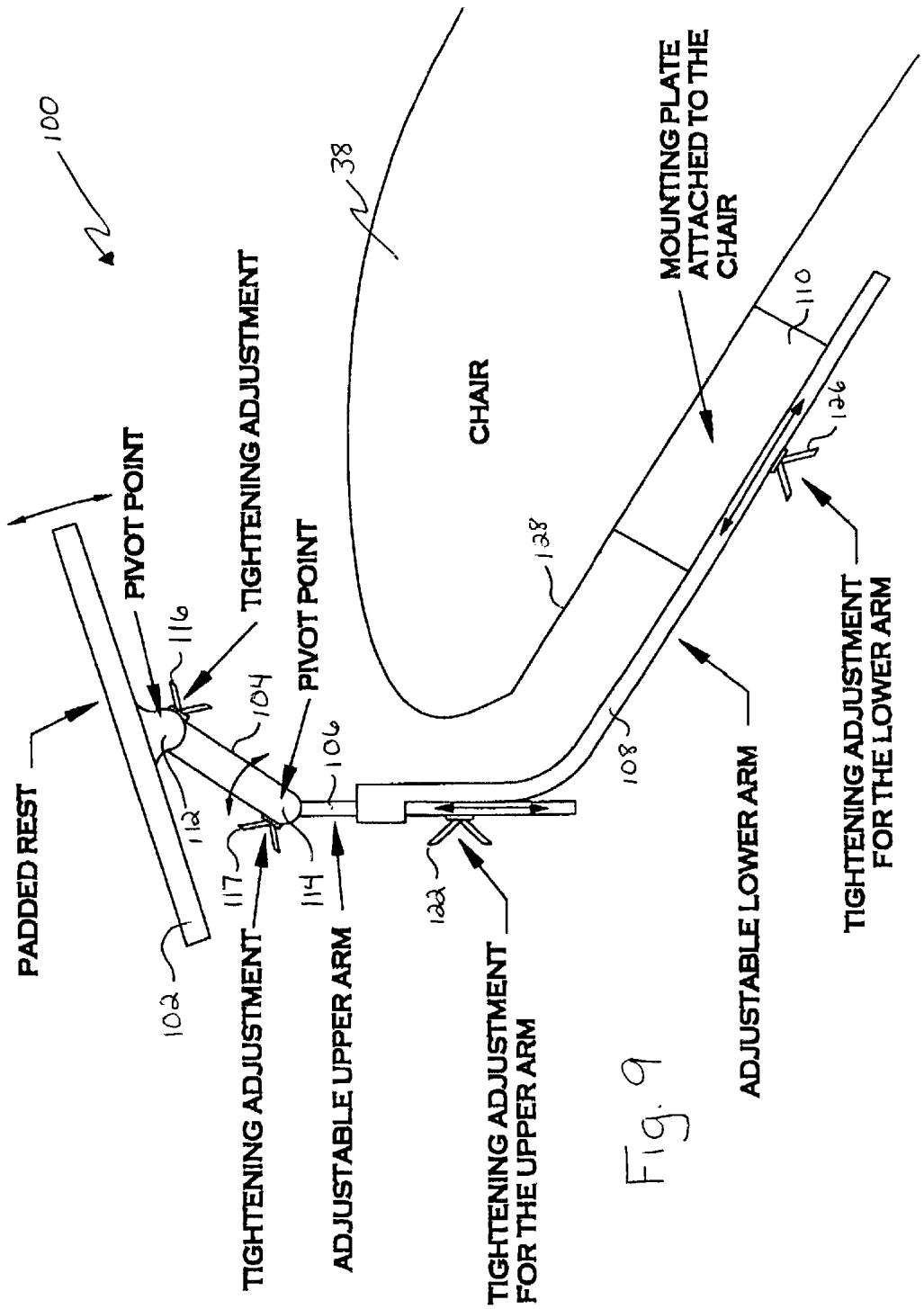
FIG. 9 is a side view of an alternate embodiment of the present invention in use with a dentist's chair.
Figure 10:
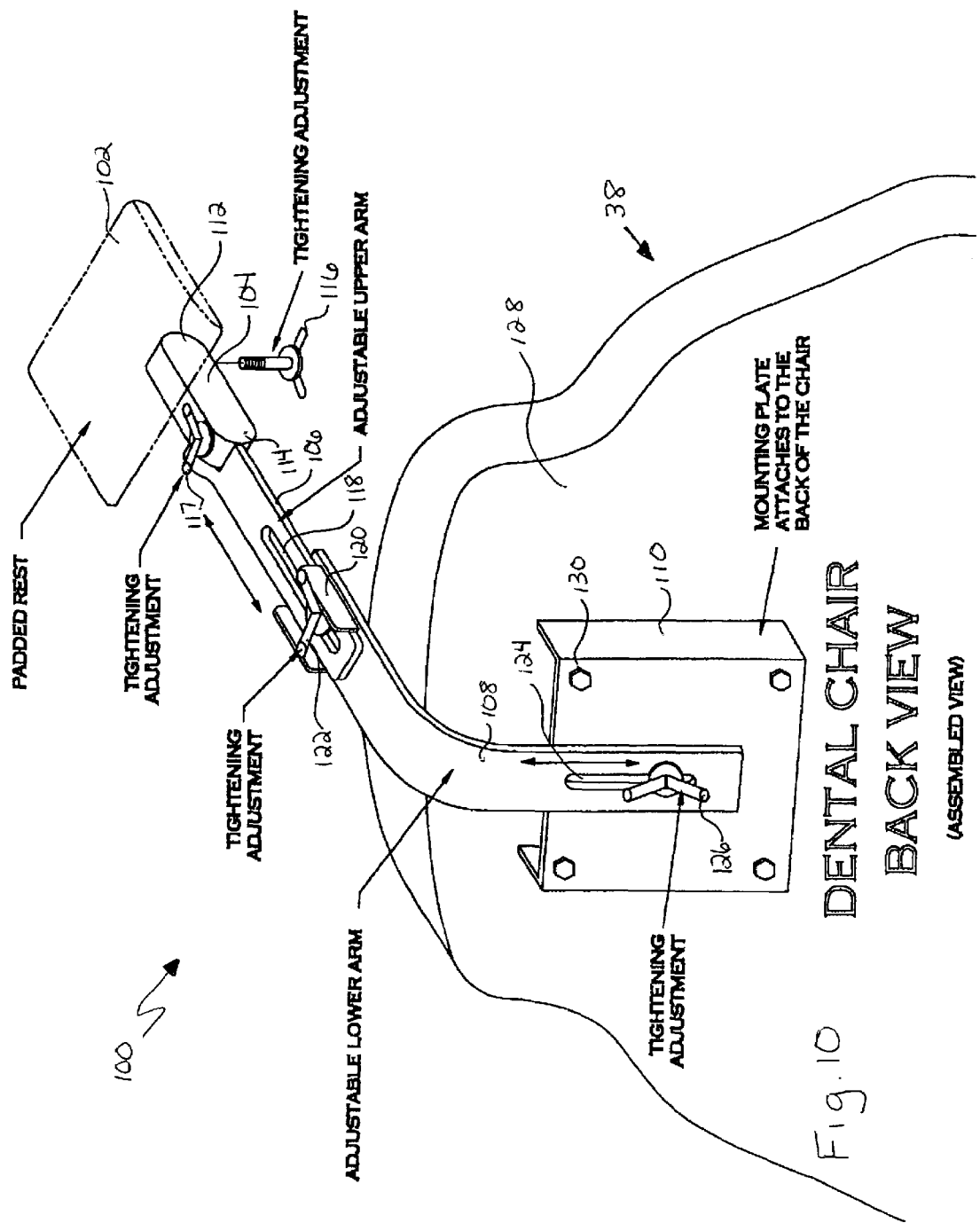
FIG. 10 is a perspective view of the device shown in FIG. 9.
Figure 11:
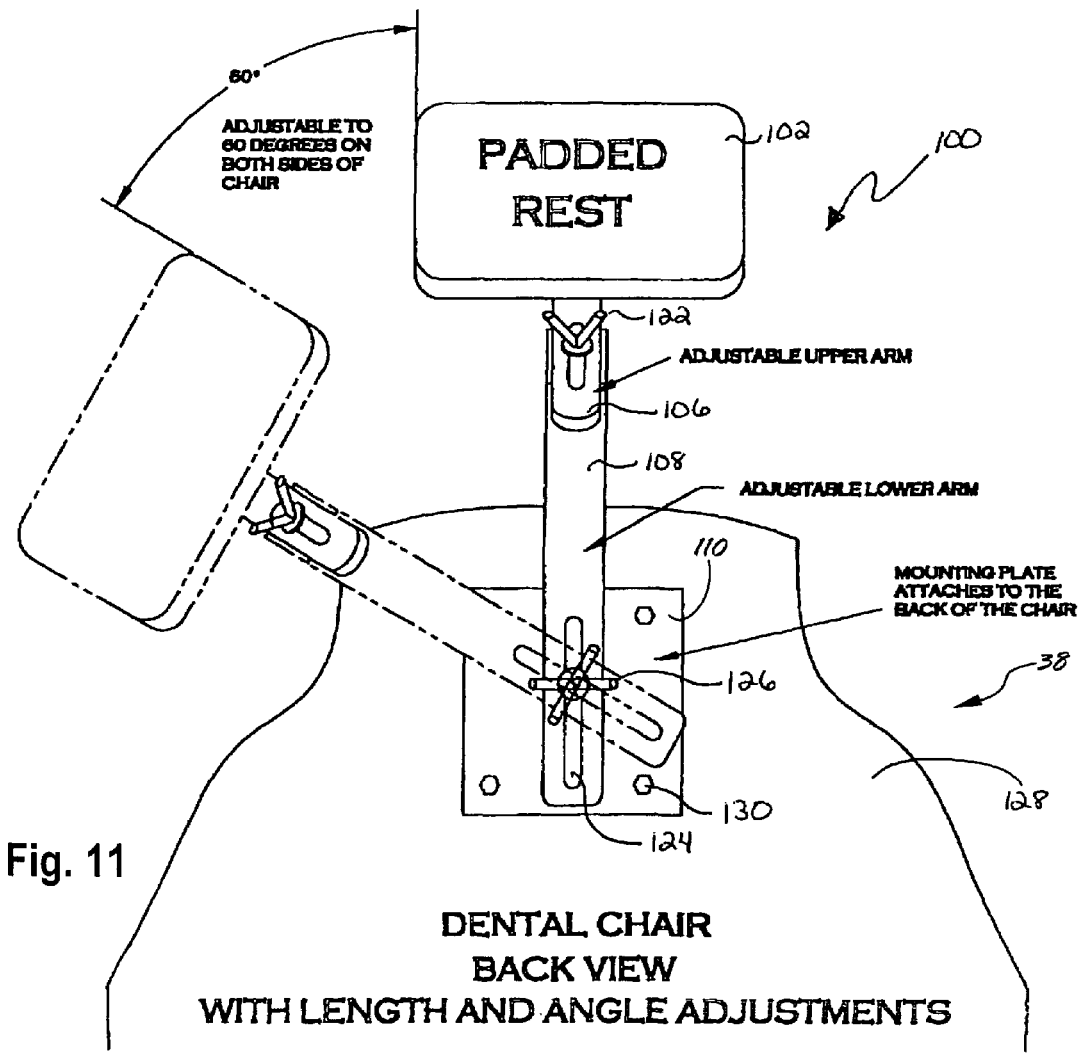
FIG. 11 is a rear view of the device shown in FIG. 9.

An alternate embodiment 100 of the present invention for use with a dental chair is shown in FIGS. 9-11. The alternate embodiment device 100 is similar to device 10 of FIG. 1, but differs in its relationship to dental chair 38. Instead of being attached to the base of dental chair 38, or to the floor, the device 100 is attached to the back 128 of the dental chair 38. As can be seen in FIG. 11, the device 100 can be rotated from one side of the dental chair 38 to the other, thereby providing flexibility by enabling the professional to work on either side of the patient. The device also allows the angle, height, and position of the rest to be adjusted, thereby providing further flexibility. Alternately, the present invention can be attached to other locations on dental chair 38, such as at a side of dental chair 38.

As depicted in FIGS. 9-11, the device 100 of this embodiment generally includes a padded rest 102, a pivot device 104, a first or upper arm 106, a second or lower arm 108, and a mounting plate 110. In this embodiment, the device 100 can be added to the dental chair 38 as an after-market item. An alternative embodiment is provided in FIG. 12, and is further described below, in which the device 100 can be provided on dental chair 38 during manufacture.

Returning to FIGS. 9-11, the padded rest 102 can be substantially the same as the padded rest 12 depicted in FIG. 1. Accordingly, the padded rest 102 can be formed in various shapes and sizes to accommodate a particular body type and gender. The padded rest 102 is attached to pivot device 104 through a first pivot point 112 proximate a first end of pivot device 104. Similarly, the first end of the upper arm 106 is attached to pivot device 104 through a second pivot point 114 proximate a second end of pivot device 104. The pivot device 104 enables the angular position of padded rest 102 to be adjusted by pivotation about pivot points 112, 114. Once the padded rest 102 has been adjusted to the desired angular position, the position of the padded rest 102 can be locked into place with a fastener 116 located at the first pivot point 112 and a fastener 117 located at the second pivot point 114. The fasteners 116, 117 are depicted in FIG. 9 as mating screws; however, the fasteners 116, 117 can be any type of screw or other coupling device. Additionally, the fastener 116 can be the same or a different type of fastener as the fastener 117. Other methods of attaching the padded rest 102 to the upper arm 106 are also possible.

The height of the device 100 can be adjusted. Providing a fastener and slot arrangement on both the upper and lower arms 106, 108 enable this feature. As can be seen in FIG. 10, a second end of the upper arm 106 is provided with a first slot 118. The second end of the upper arm 106 is guided along rails 120 provided on a first end of the lower arm 108. Once the desired height is obtained, a fastener 122 is inserted into the first slot 118 and into a hole provided on the first end of the lower arm 108, thereby securing the upper arm 106 at the desired height with respect to the lower arm 108. The fastener 122 is depicted in FIGS. 9-12 as a mating screw; however, the fastener 122 can be any type of screw or other coupling device. Other methods of attaching the upper arm and lower arm, 106, 108 are possible.

Similarly, a second end of the lower arm 108 is provided with a second slot 124 which cooperates with a fastener 126 to mount the lower arm 108 to the mounting plate 110 provided on the back 128 of the dental chair 38. The fastener 126 is depicted in FIGS. 9-11 as a mating screw; however, the fastener 126 can be any type of screw or other coupling device. Additionally, the fastener 126 can be the same or a different type of fastener as fastener 122.

To adjust the position of device 100 with respect to chair 38, fastener 126 is loosened, the position of lower arm 108 with respect to chair 38 is adjusted and fastener 126 is again tightened. Other methods of attaching lower arm 108 and mounting bracket 110 are possible.

It is the slot and screw arrangement provided on the second end of the lower arm 108 which enables device 100 to be rotated, from one side of dental chair 38 to the other. In a preferred embodiment, device 100 can rotate 120 degrees from one side of dental chair 38 to the other. However, device 100 is not limited to that range of motion.

As can be appreciated from FIG. 11, to adjust the angular position of device 100, fastener 126 is loosened, the angular position of device 100 is adjusted (as shown in the dotted lines), and fastener 126 is again tightened. Thus, this arrangement allows device 100 to be locked at each position, thereby providing flexibility by enabling the professional to work on either side of the patient. At the same time the angular position of device 100 is adjusted, the height of device 100 can also be adjusted by sliding lower arm 108 along slot 124 and tightening fastener 126 once the desired height is obtained.

The device 100 can be mounted to the dental chair 38 via a mounting plate 110. FIGS. 9-11 show the mounting plate 110 attached to the back 128 of the dental chair 38; however other mounting locations are possible, such as a side of the dental chair 38. While the mounting plate 110 is depicted in FIGS. 10-11 as being positioned substantially in the center of back 128 relative to the sides of dental chair 38, mounting plate 110 can be positioned anywhere on back 128 of the chair.

The mounting plate 110 can be fastened to back 128 of dental chair 38 with a plurality of fasteners 130, such as screws. FIG. 10 depicts mounting plate 110 being fastened to back 128 of dental chair 38 with four screws; however, the number and type of fasteners can vary.

Figure 12:
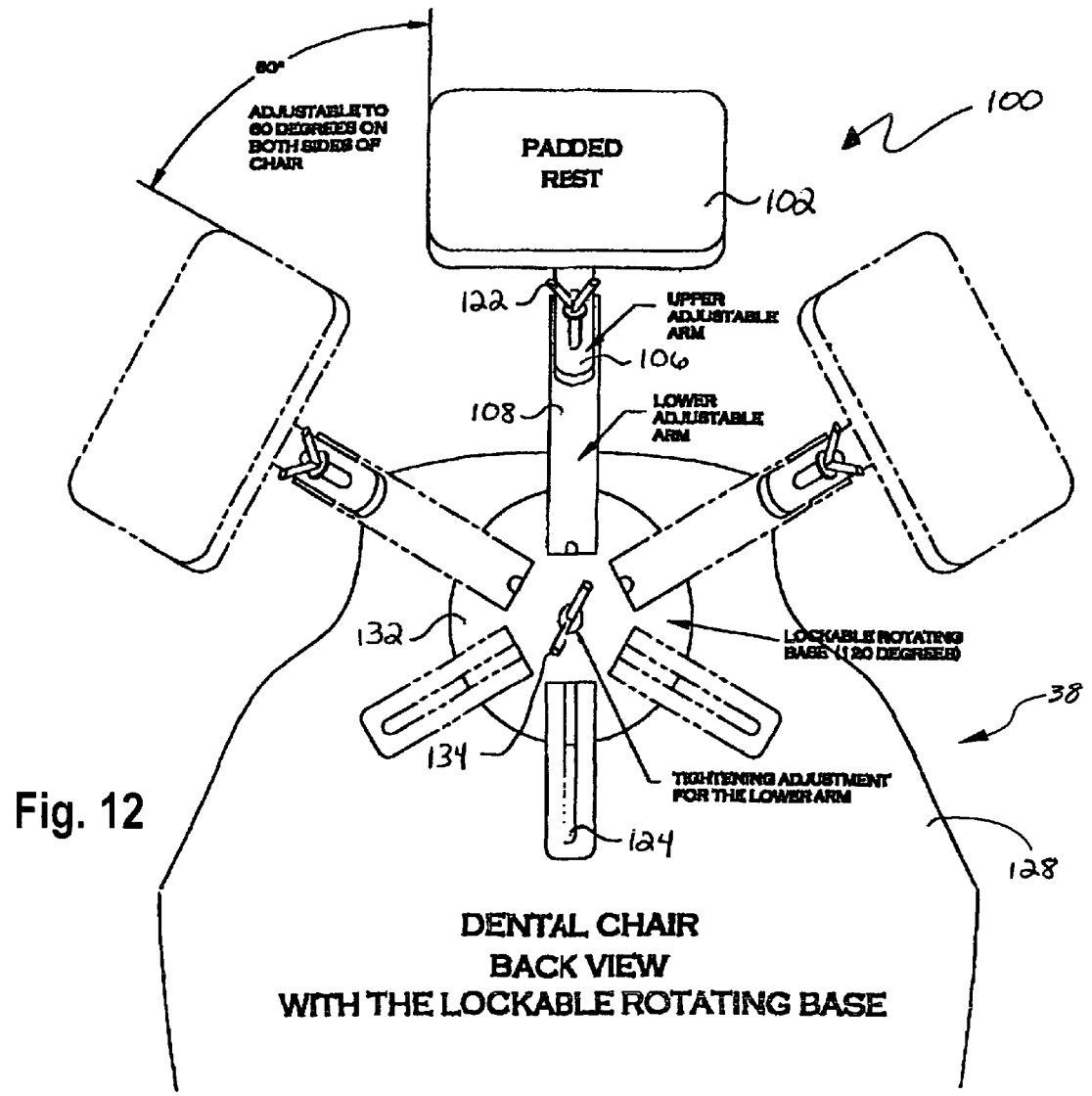
FIG. 12 is a rear view of an alternative embodiment of the present invention in use with a dentist's chair.

FIG. 12 provides an alternative third embodiment for mounting device 100 to dental chair 38. In this embodiment, device 100 can be provided on dental chair 38 during original equipment manufacture of the chair as well as being available as an after-market product. Accordingly, instead of using a mounting bracket 110, device 100 is attached to back 128 of dental chair 38 using a rotatable base 132. The rotatable base 132 can be integral with dental chair 38 or can be a separate device added to dental chair 38 during manufacture.

While rotatable base 132 is depicted in FIG. 12 as being positioned substantially in the center of back 128 relative to the sides of dental chair 38, rotatable base 132 can be positioned anywhere on back 128. Additionally, rotatable base 132 can be attached to other locations on dental chair 38, such as a side of dental chair 38.

The rotatable base 132 comprises rotation structure which enables device 100 to be rotated (as shown in the dotted lines), from one side of dental chair 38 to the other. In a preferred embodiment, device 100 can rotate 120 degrees from one side of dental chair 38 to the other. However, device 100 is not limited to that range of motion.

At the same time the angular position of device 100 is adjusted, the height of device 100 can also be adjusted by sliding lower arm 108 along slot 124. In this embodiment, a fastener 134 enables device 100 to be locked at each position, thereby providing flexibility by enabling the professional to work on either side of the patient. The fastener 134 is depicted in FIG. 12 as a mating screw; however, fastener 134 can be any type of screw or other coupling device. Other methods of locking device 100 into position are possible.

FIGS. 1, 2, 6, 7*a*, 7*b*, and 8-12 illustrate use of the support device 10, 100 with a medical patient chair, for treating a medical patient in the chair, the chair inherently having a projected perimeter when considered in plan view. The embodiments of FIGS. 1, 2, 6, 7*a*, 7*b*, and 8 illustrate lateral adjustment of the support device along that portion of the projected perimeter which extends along a side of the chair. The embodiments of FIGS. 9-12 illustrate lateral adjustment of the support device along that portion of the projected perimeter which extends about the back of the medical chair.

The present invention is not limited to use in the dental setting. Such a device can be beneficial in other fields in which the individuals spend much of their day in the forward bent position. For example, a lab technician who spends much of the day leaning over a bench can benefit from the present invention. in addition, the present invention can be helpful to others, such as individuals who lean forward over a countertop, desktop or work bench during the course of the day.

Figure 4:
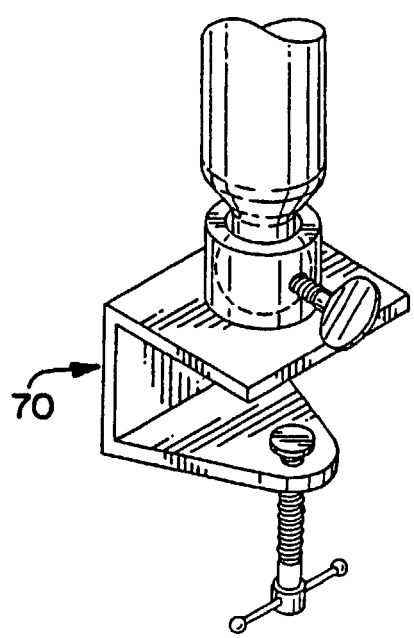
FIG. 4 is a perspective view of an alternate attachment for the embodiment of FIG. 3.

For example, FIG. 3 depicts an alternate embodiment 48 of the present invention in use with a desk, table or workbench 50. The embodiment 48 generally comprises a padded rest 52 and an upright bracket 54. To adjust the angle of the rest 52, a ball swivel (not shown) with a screw pivot (not shown), as depicted in FIG. 6, is provided between rest 52 and bracket 54. The bracket 54 is also provided with the telescoping feature of FIGS. 7*a* and 7*b*, thereby making it adjustable in height. To allow the horizontal lateral position of the bracket 54 with respect to the desk 50 to be adjusted, the lower end of the bracket 54 is provided with a slide member 62 and desk 50 is provided with a track member 64. The slide member 62 rides along track member 64 in a conventional manner. To lock bracket 54 in a certain position along track 64, a pivot 68 is engaged. Alternately, the lower end of the bracket 54 can be provided with a [A]C-clamp[@] type mount 70, as shown in FIG. 4. Such clamp 70 along with a ball joint pivot can mount the device directly to the edge of the desk or workbench 50.

Figure 5:
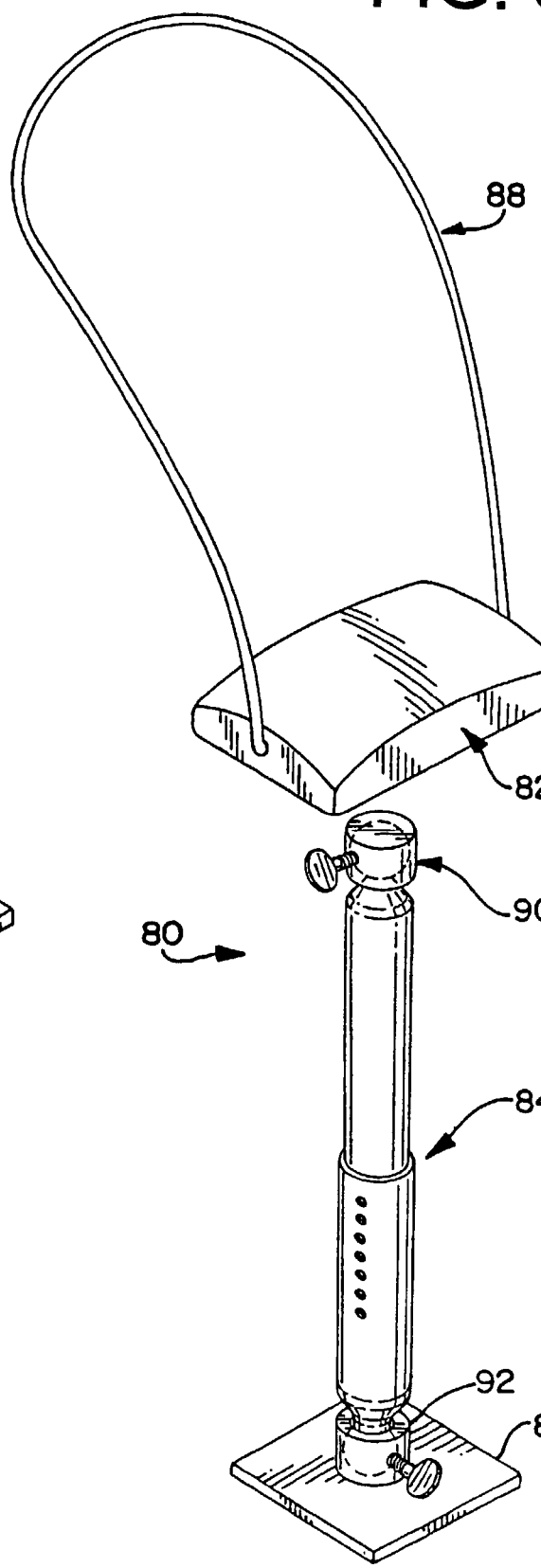
FIG. 5 is a partially exploded, perspective view of another alternate embodiment of the present invention for use in activities such as gardening.

FIG. 5 depicts yet a further embodiment 80 of the present invention for use in gardening or activities involving kneeling. Such a device can include a padded rest 82, a vertical adjustable bracket 84, and a footplate 86 at the lower end of bracket 84. A neck or shoulder strap 88 can be attached to the support device, as shown at padded rest 82, for carrying the device thereby allowing the user to change positions without the use of his hands.

The device can be provided with a coupling 90 between rest 82 and bracket 84 to vary the angle of rest 82 with respect to bracket 84. In addition, a coupling 92 can also be provided between bracket 84 and footplate 86. These couplings can take the form of a ball swivel with a screw pivot, similar to that shown in FIG. 6. The bracket 84 can also be provided with the telescoping feature, shown in FIGS. 7*a* and 7*b*, to enable the height of the bracket 84 to be adjusted.

While the invention has been described in connection with certain embodiments, it should be understood that it is not intended to limit the invention to these particular embodiments. To the contrary, it is intended to cover all alternatives, modifications and equivalents falling within the spirit and scope of the invention.

The invention claimed is:

1. A support device adapted to be used with a medical patient chair, said medical patient chair having a back and a projected perimeter, said support device comprising:
   a) a padded rest which a user, who is not a patient seated in said medical patient chair, can lean his torso against; and
   b) a support structure adapted to support said padded rest from a mounting plate securable to said back of said medical patient chair, said support structure providing for adjustment of said padded rest and comprising:
(i) a first apparatus enabling height adjustment of said padded rest, said first apparatus including a first arm having a first slot formed therethrough and a second arm having a hole formed therein, said first arm being movable relative to said second arm and capable of being secured in a desired position by a first fastener which passes through said first slot and into said hole;
(ii) a second apparatus enabling adjustment of said padded rest toward or away from said medical patient chair, said second apparatus including a second slot formed in said second arm, said second arm being movable relative to said mounting plate and capable of being secured in a desired position by a second fastener which passes through said second slot and into said mounting plate; and
(iii) a third apparatus enabling angular orientation of said padded rest relative to said medical patient chair, said third apparatus including said second slot and said second fastener whereby said second arm can be angularly rotated relative to said mounting plate and is capable of being secured in a desired angular position by said second fastener;

said support structure being adapted for positioning said padded rest so as to enable said user to position his torso against said padded rest while working on a patient seated in said medical patient chair, such that said padded rest bears substantial weight of said user's torso.

2. The support device of claim 1 wherein said padded rest can rotate 120 degrees.

3. The support device of claim 2 wherein said padded rest can rotate 60 degrees from a vertical central axis of said medical patient chair.

4. The support device of claim 1 wherein said second arm is bent.

5. The support device of claim 1 wherein said mounting plate is rotatable.

6. The support device of claim 5 wherein said rotatable base enables said support structure to be locked in a desired position of rotation relative to said projected perimeter of said medical patient chair.

7. A support device adapted to be used with a medical patient chair, said medical patient chair having a back and a projected perimeter, said support device comprising:
a) a padded rest which a user, who is not a patient seated in said medical patient chair, can lean his torso against; and
b) a support structure adapted to support said padded rest from a mounting plate securable to said back of said medical patient chair, said support structure providing for adjustment of said padded rest and comprising:
(i) a first apparatus enabling height adjustment of said padded rest, said first apparatus including a first arm having a first slot formed therethrough and a second arm having a hole formed therein, said first arm being movable relative to said second arm and capable of being secured in a desired position by a first screw fastener which passes through said first slot and into said hole;
(ii) a second apparatus enabling adjustment of said padded rest toward or away from said medical patient chair, said second apparatus including a second slot formed in said second arm and spaced away from said hole, said second arm being movable toward or away from said mounting plate and capable of being secured in a desired position by a second screw fastener which passes through said second slot and into said mounting plate; and
(iii) a third apparatus enabling angular orientation of said padded rest relative to said medical patient chair, said third apparatus including said second slot and said second screw fastener whereby said second arm can be angularly rotated relative to said mounting plate and is capable of being secured in a desired angular position by said second screw fastener;

said support structure being adapted for positioning of said padded rest so as to enable said user thereof to position his torso against said padded rest while working on a patient seated in said medical patient chair, such that said padded rest bears substantial weight of said user's torso.

8. The support device of claim 7 wherein said padded rest can rotate 120 degrees.

9. The support device of claim 7 wherein said mounting plate is rotatable.

10. The support device of claim 7 wherein said second arm is bent.

11. A support device adapted to be used with a table, said support device comprising:
a) a padded rest which a user can lean his torso against;
b) a support structure adapted to support said padded rest from a base, and relative to said table, said support structure providing for adjustment of said padded rest and comprising:
(i) an apparatus enabling height adjustment of said padded rest, said apparatus including a bracket with said padded rest attached to a first end of said bracket;
(ii) an apparatus enabling adjustment of said padded rest toward or away from said table; and
(iii) an apparatus enabling angular orientation of said padded rest relative to said table;

said support structure comprising a slide member positioned approximate a second end of said bracket, and an elongate track member having a length and being adapted and configured to be mounted to said table so as to receive said slide member, and to accommodate riding of said slide member along at least a portion of the length of said table, said support structure being adapted for positioning of said padded rest so as to enable said user to position his torso against said padded rest while working on an object on said table such that said padded rest can bear substantial weight of said user's torso.

12. The support device of claim 11 wherein said apparatus enabling angular orientation of said padded rest comprises a ball with a screw pivot.

13. The support device of claim 11 wherein said apparatus enabling angular orientation of said padded rest serves as an interface between said padded rest and said bracket.

14. A support device adapted to be used with a medical patient chair, said medical patient chair having a back and a projected perimeter, said support device comprising:
a) a padded rest which a user, who is not a patient seated in said medical patient chair, can lean his abdominal, chest or anterior shoulder areas against; and
b) a support structure adapted to support said padded rest from a mounting plate securable to said back of said medical patient chair, said support structure providing for adjustment of said padded rest and comprising:
(i) a first apparatus enabling height adjustment of said padded rest, said first apparatus including a first arm having a first slot and a second arm having a second slot, said first arm being movable relative to said second arm and secured thereto in a desired position by a first fastener;

(ii) a second apparatus enabling adjustment of said padded rest across said projected perimeter and thereby enabling adjustment of said padded rest toward or away from said medical patient chair; and (iv) a third apparatus enabling angular orientation of said padded rest relative to said medical patient chair, said third apparatus including a rotatable base secured to said medical patient chair and a second fastener which cooperates with said second slot formed in said second arm;

said support structure being adapted for positioning said padded rest so as to enable said user to position his abdominal, chest or anterior shoulder areas against said padded rest while working on a patient seated in said medical patient chair such that said padded rest bears substantial weight of said user's abdominal, chest or anterior shoulder areas.

* * * * *